United States Patent [19]

Barnes III

[11] Patent Number: 5,563,112

[45] Date of Patent: Oct. 8, 1996

[54] HERBICIDAL DIPHENYL ETHER AND NITROGEN SOLUTION COMPOSITIONS AND METHOD

[75] Inventor: Clyde J. Barnes III, Champaign, Ill.

[73] Assignee: Zeneca Limited, London, England

[21] Appl. No.: 487,714

[22] Filed: Jun. 7, 1995

Related U.S. Application Data

[63] Continuation of Ser. No. 173,340, Dec. 22, 1993, abandoned.

[51] Int. Cl.$^6$ ............................. A01N 25/32; A01N 41/06
[52] U.S. Cl. ...................... 504/125; 504/149; 504/333; 504/334; 504/103; 504/148
[58] Field of Search .................................. 504/123, 125, 504/148, 149, 333, 334, 103

[56] References Cited

U.S. PATENT DOCUMENTS

| | | | |
|---|---|---|---|
| 4,285,723 | 8/1981 | Cartwright et al. | 504/333 |
| 4,851,034 | 7/1989 | Claus | 504/333 |

FOREIGN PATENT DOCUMENTS

| | | |
|---|---|---|
| 0243522 | 11/1987 | European Pat. Off. |
| 0317260 | 5/1989 | European Pat. Off. |
| 3226534 | 2/1983 | Germany |
| 264837 | 2/1989 | Germany |
| 9007275 | 7/1990 | WIPO |

OTHER PUBLICATIONS

Felding et al. "Effects of Additives on Efficacy . . . " Weed Tech., 1990, vol. 4, pp. 264–271.
Martin, "Fertilizer Additives with Postemergence Soybeantlerbicide", Proc. North Cent. Weed Control Conf., 1987, 42:42.
Mohan et al., "Addition of Spray Adjuvants . . . ", Proc. North Cent. Weed Control Conf., 1986, 41:45.
Chemical Abstracts, vol. 119 No. 1, Jul. 5, 1993, Columbus, OH, Abstr: 2968, S. Gara et al. "Weed Control of soybean and pea by Pivot 100 EC at reduced rates and supplemented with adjuvants" *Novenyvedelem*, vol. 28, No. 12, 1992, Budapest, Hu pp. 524–530.
Chemical Abstracts, vol. 117, No. 11, Sep. 14, 1992, Columbus, OH, Abstr: 106231, K. A. Renner et al. "Response of navy bean (Phaseolus vulgaris) and wheat (Triticum aestivum) grown in rotation to clomazone, imazethapyr, bentazon, and acifluorfen" *Weed Sci.*, vol. 40, No. 1, 1992, pp. 127–133.

Farm Chemicals Handbook '92, PS B–23.

Fielding, Robert J. et al., "Effects of Additives on Efficacy, Uptake, and Translocation of Chlorimuron Ethyl Ester[1] ", Weed Technology, 1990, vol. 4, pp. 264–271.

Koppatschek, F. R. Liebl and L. Wax, "Fertilizer Additives For Acifluorfen and Bentazon", Proc. North Cent. Weed Control Conf. 1986, 41:46.

Lueschen, W. E. and T. R. Hoverstad, "Soybean Injury and Weed Control As Influenced by Additives for Postemergence Herbicides", Proc. North Cent. Weed Control Conf., 1986, 41:55.

Martin, A. R., "Fertilizer Additives with Postemergence Soybean Herbicide", Proc. North Cent. Weed Control Conf., 1987, 42:42.

Mitchell, J. W. and P. J. Linder, "Absorption and Translocation of Radioactive 2,4–DI by Bean Plants as Affected by Cosolvents and Surface Agents", Science, 1950, 112:54–55.

Mohan, R. G. and D. P. Rathmann, "Addition of Spray Adjuvants and 2,4–DB to Acifluorfen, Bentazon and Fertilizer Combinations in Soybeans", Proc. North Cent. Weed Control Conf., 1986, 41:45.

*Primary Examiner*—José G. Dees
*Assistant Examiner*—Brian G. Bembenick
*Attorney, Agent, or Firm*—Marian T. Thomson

[57] ABSTRACT

A herbicidal composition comprising herbicidally effective amounts of a diphenyl ether of the formula

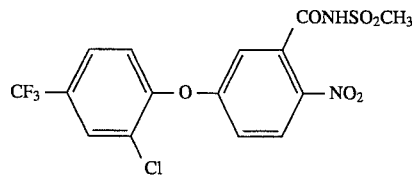

at least one nitrogen containing fertilizer that is present in an amount that increases the herbicidal activity of said diphenyl ether; and one or more adjuvants.

7 Claims, No Drawings

HERBICIDAL DIPHENYL ETHER AND NITROGEN SOLUTION COMPOSITIONS AND METHOD

This application is a continuation of application Ser. No. 08/173,340, filed Dec. 22, 1993 (Abandoned).

BACKGROUND OF THE INVENTION

In many cases, novel mixtures of known agrochemicals have been shown to be more effective in combination than when applied individually. The present invention resides in the discovery of novel herbicidal compositions which comprise herbicidally effective amounts a diphenyl ether, nitrogen sources and adjuvants.

The invention also comprises a method of controlling undesirable vegetation in the presence of a crop, particularly a soya crop, by applying to the locus of the crop or undesired vegetation a herbicidal composition comprising herbicidally effective amounts of the diphenyl ether, the nitrogen source, and one or more adjuvants.

PRIOR ART

The compounds forming the combination which is the subject of the present invention are independently known in the art for their effects on plant growth. Diphenyl ethers such as fomesafen are disclosed as herbicides in U.S. Pat. No. 4,285,723. Nitrogen is well known in the art as a fertilizer and is described in the Farm Chemicals Handbook, 1992 Edition on page B23. Commercially available nitrogen fertilizers include anhydrous ammonia, ammonium nitrate, ammonium sulfate, urea, nitrogen solutions (which include urea ammonium nitrate), ammonium phosphate, potassium nitrate, and combinations thereof. Other fertilizers include methyl ammonia, ammonia chloride and methyl ammonia chloride. Other compounds used in the herbicidal composition of this invention are adjuvants. The term adjuvant includes materials such as wetting agents, spreaders, emulsifiers, dispersing agents, crop oil concentrates, surfactants and the like.

DESCRIPTION OF THE INVENTION

It has been discovered that the control of undesirable vegetation is exhibited by compositions comprising a mixture of the following compounds:

a) an herbicidally effective amount of a substituted diphenyl ether known as fomesafen

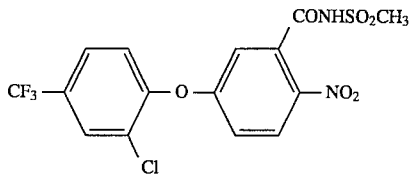

b) at least one nitrogen containing fertilizer that is present in an amount that increases the herbicidal activity of said diphenyl ether; and c) one or more adjuvants.

Fomesafen is disclosed in U.S. Pat. No. 4,285,723. Processes for its preparation are also disclosed in the same patent which is hereby incorporated by reference.

Nitrogen sources used in fertilizing materials are commonly classified as either nitrate or ammonium types. Commercially available ammonium types include anhydrous ammonia, aquaammonia, ammonium nitrate, ammonium sulfate, fluid nitrogen fertilizers, urea, and ammonium phosphates. The nitrate type fertilizers include ammonium nitrate, nitrogen solutions, calcium nitrate and sodium nitrate. The preferred nitrogen fertilizers are nitrogen solutions. The most preferred nitrogen fertilizer is urea ammonium nitrate (UAN) wherein the % N is about between 28–33%. This solution and other nitrogen solutions within the scope of the present invention can be prepared by known procedures in the art.

The preferred adjuvants include crop oil concentrates, nonionic, anionic, cationic and amphoteric surfactants.

Crop oil concentrates are available from a variety of sources, and generally consist of from 65–95 percent by weight of a hydrocarbon oil or solvent with the balance being a surfactant. The hydrocarbons which form the bulk of the crop oil concentrate may be derived from mineral (petroleum) or vegetable sources. Examples of vegetable oils include oils from seeds of crops such as sunflower.

Examples of anionic surfactants include:

a) carboxylic acid salts, for example, sodium and potassium salts of coconut oil fatty acids;

b) sulfonic acid salts, for example, linear alkyl benzene sulfonates, sodium, calcium and ammonium lignosulfonates, petroleum sulfonates, paraffin sulfonates, and alkyl naphthalene sulfonates;

c) sulfuric acid ester salts, for example, sulfated linear primary alcohols; and d) phosphonic and polyphosphonic acid esters, for example, sodium alkyl phosphate (not oxyethylenated).

Examples of cationic surfactants include:

a) long chain amines;

b) quaternary ammonium salts, for example, cetyltrimethyl ammonium bromide and N-alkyl trimethyl ammonia chloride; and c) polyoxyethylenated long chain amines.

Examples of nonionic surfactants include:

a) polyoxyethylenated alkyl phenols;

b) polyoxyethylenated straight-chain alcohols;

c) polyoxyethylenated polyoxypropylene glycols;

d) glyceryl and polyglyceryl esters of natural fatty acids;

e) propylene glycol, sorbital polyoxyethylenated sorbital esters;

f) alkanolamines;

g) tertiary acetylenic glycols;

h) polyoxyethylenated silicones;

i) N-alkyl pyrrolidones; and j) alkyl polyglycosides.

Examples of ampholytic surfactants include:

a) β-N-alkylaminopropionic acids;

b) N-alkyl-β-iminodipropionic acids;

c) imidazoline carboxylates;

d) N-alkylbetaines;

e) amino oxides;

f) sulfobetaines or sultaines; and g) phosphatides.

These surfactants and others are described in Drew Myers, *Surfactant Science and Technology*, (New York: VCH Publishers, Inc., 1988), Chapter 2 and Milton J. Rosen, *Surfactants and Interfacial Phenomena,* 2nd Edition, (New York: John Wiley and Sons, Inc., 1989), Chapter 1.

Exemplary adjuvants found to be useful in the compositions of this invention include the following: polyoxyethylene sorbitan monolaurates, manufactured by ICI Americas Inc. and sold under the tradename Tween 20; alkylaryl-polyoxyethylenes, manufactured by Chevron Chemical Co. and sold under the tradename Ortho X-77; paraffin based petroleum oil, polyoxyethylated polyol fatty acids and polyol fatty esters, manufactured by Helena Chemical Co. and sold under the tradename Agridex; DASH, a tradename of a proprietary blend of surfactants manufactured by BASF Corporation; crop oil concentrate; and silicone based additives.

In addition to the foregoing, inert adjuvants can also be incorporated into the compositions of this invention to provide a more satisfactory formulation. Such inert adjuvants include spreaders, emulsifiers, dispersing agents, foaming adjuvants, foam suppressants, penetrants and correctives.

Particularly preferred adjuvants are crop oil concentrates, especially vegetable oil/surfactant combinations such as SCOIL® which is a methylated sunflower oil adjuvant containing 30% nonionic surfactant.

The term herbicide is used herein to denote a compound which controls or modifies the growth of plants. The term herbicidally effective amount is used to indicate the quantity of such compound or combination of such compound which is capable of producing a controlling or modifying effect. Controlling or modifying effects include all deviations from natural development, for example: killing, retardation, leaf burn, dwarfing and the like. The term plants is used to include all postemergent vegetation, ranging from seedlings to established vegetation.

The term nitrogen fertilizer is used herein to denote a primary nutrient that is required by all plants in considerable quantities for plant growth. Certain fertilizers have been used by applicators as carriers for pesticides. This type of application method allows the grower to apply the nitrogen and herbicide at the same time in one operation. The benefits of this system are reduced time and labor needs.

Application rates will depend upon the weeds to be controlled and the degree of control desired. In general, the compositions of this invention are most efficiently employed at a rate of 0.001 to 20 pounds per acre (0.001 to 22.4 kilograms per hectare) of the active ingredients, preferably 0.01 to 15 pounds per acre (0.01 to 16.8 kilograms per hectare).

Usually, the nitrogen source and adjuvants are added independently to the spray mixture as a percent of the total spray volume or as gallons of product per acre. A preferred application range is 0.001 to 200 gallons of product per acre, more preferably about 0.01 to 5.0 gallons of product per acre, and most preferably about 0.1 to 2 gallons of product per acre for UAN and adjuvants.

Herbicidal Evaluations

Herbicidal evaluations of mixtures of fomesafen, UAN and SCOIL®.

EXAMPLE I

This example demonstrates the effect of fomesafen, urea ammonium nitrate (UAN) and SCOIL® in combined postemergence application on a variety of weeds.

The weed species were as follows:

| Abbreviation | Common Name | Scientific Name | Growth Stage |
|---|---|---|---|
| IS | morningglory | Ipomoea sp. | 7 leaf* |
| AT | velvetleaf | Abutilon theophrasti | 6–7 leaf |
| XS | cocklebur sp. | Xanthium sp. | 6–7 leaf |
| The crop species were as follows: | | | |
| SO | soybean | | 3rd trifoliate |

*cut above leaf number 4 before spraying

Fomesafen, formulated as Reflex 2LC, was applied by postemergence application to soybean, (variety Williams 82), morningglory, velvetleaf and cocklebur at 140 l/ha. SCOIL® and UAN were added by tank mixing as detailed in the Tables.

The Tables give the results of assessments made at 4, 14 and 21 DAT (days after treatment). The injury rating on a scale of 0 to 100% was recorded for each species as percent control with 0% representing no injury and 100% complete kill.

TABLE I

4 DAT

| Adjuvant | Rate g ai/ha | % Injury SO | % Control | | |
|---|---|---|---|---|---|
| | | | AT | XS | IS |
| None | 50 | 0 | 13 | 33 | 18 |
| None | 75 | 7 | 20 | 63 | 35 |
| None | 100 | 2 | 18 | 66 | 35 |
| S @ 0.25% | 50 | 18 | 60 | 83 | 97 |
| S @ 0.25% | 75 | 11 | 50 | 88 | 96 |
| S @ 0.25% | 100 | 15 | 70 | 83 | 91 |
| S @ 0.5% | 25 | 18 | 75 | 88 | 89 |
| S @ 0.5% | 50 | 25 | 85 | 91 | 88 |
| S @ 0.5% | 75 | 18 | 78 | 91 | 92 |
| S @ 0.5% + UAN @ 4% | 25 | 18 | 85 | 93 | 97 |
| S @ 0.5% + UAN @ 4% | 50 | 9 | 96 | 94 | 98 |
| S @ 0.5% + UAN @ 4% | 75 | 8 | 95 | 95 | 98 |

* S is SCOIL®
* UAN is urea ammonium nitrate

TABLE II

14 DAT

| Adjuvant | Rate g ai/ha | % Injury SO | % Control | | |
|---|---|---|---|---|---|
| | | | AT | XS | IS |
| None | 50 | 0 | 5 | 17 | 12 |
| None | 75 | 0 | 10 | 37 | 16 |
| None | 100 | 0 | 10 | 50 | 26 |
| S @ 0.25% | 50 | 0 | 15 | 42 | 63 |
| S @ 0.25% | 75 | 0 | 23 | 50 | 70 |
| S @ 0.25% | 100 | 0 | 18 | 53 | 65 |
| S @ 0.5% | 25 | 0 | 23 | 40 | 65 |
| S @ 0.5% | 50 | 0 | 27 | 45 | 65 |
| S @ 0.5% | 75 | 0 | 20 | 50 | 72 |
| S @ 0.5% + UAN @ 4% | 25 | 0 | 40 | 33 | 75 |
| S @ 0.5% + UAN @ 4% | 50 | 0 | 73 | 63 | 88 |
| S @ 0.5% + UAN @ 4% | 75 | 0 | 47 | 90 | 98 |

TABLE III

| | | 21 DAT | | | |
|---|---|---|---|---|---|
| | Rate | % Injury | % Control | | |
| Adjuvant | g ai/ha | SO | AT | XS | IS |
| None | 50 | 0 | 3 | 7 | 5 |
| None | 75 | 0 | 0 | 20 | 11 |
| None | 100 | 0 | 0 | 28 | 8 |
| S @ 0.25% | 50 | 0 | 2 | 18 | 40 |
| S @ 0.25% | 75 | 0 | 0 | 17 | 42 |
| S @ 0.25% | 100 | 0 | 2 | 32 | 38 |
| S @ 0.5% | 25 | 0 | 7 | 25 | 25 |
| S @ 0.5% | 50 | 0 | 5 | 25 | 55 |
| S @ 0.5% | 75 | 0 | 0 | 22 | 43 |
| S @ 0.5% + UAN @ 4% | 25 | 0 | 22 | 18 | 47 |
| S @ 0.5% + UAN @ 4% | 50 | 0 | 42 | 42 | 65 |
| S @ 0.5% + UAN @ 4% | 75 | 0 | 13 | 80 | 95 |

As shown by the data in Tables I–III, the addition of SCOIL® and UAN did not increase soya injury after the first assessment. The analysis reveals that the combination of fomesafen, UAN and adjuvant has a different degree of effectiveness on various weed species, but it is clear that the addition of UAN and SCOIL® increases weed control by fomesafen across all tested weed species at all rates tested.

Formulations

The compounds and compositions of this invention can be formulated in the same manner in which herbicides are generally formulated. The object of the formulation is to apply the compounds and compositions to the locus where control is desired by conventional method. The locus may include soil, seeds, seedlings, crop, crop seeds and vegetation.

Useful formulations of the compounds of this invention can be prepared in conventional ways. They include dusts, granules, microcapsules, pellets, solutions, suspensions, emulsions, wettable powders, emulsifiable concentrates and the like. Many of these may be applied directly to the locus. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active herbicide and optionally antidote ingredient(s) and optionally at least one of (a) about 0.1% to 20% surfactant(s) and (b) about 1% to 99.9% solid or liquid inert diluent(s). More specifically, they can contain these ingredients in the following approximate proportions.

TABLE IV

| | Herb. & Ant. | Active Weight Percent * | |
|---|---|---|---|
| | Ingredients | Diluent(s) | Surfactant(s) |
| Wettable Powders | 20–90 | 0–74 | 1–10 |
| Oil Suspensions Emulsions, Solutions (Including Emulsifiable Concentrates) | 3–50 | 40–95 | 0–15 |
| Aqueous Suspension | 10–50 | 40–84 | 1–20 |
| Dusts | 1–25 | 70–99 | 1–20 |
| Granules and Pellets | 0.1–95 | 5–99.9 | 0–15 |
| Compositions | 90–99 | 0–10 | 0–2 |

* Active ingredient plus at least one of a Surfactant or a Diluent equals 100 weight percent.

Lower or higher levels of active ingredient can be present depending on the intended use.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anticaking and anti-static agents may also be added. Dusts may be applied by spraying from boom sprayers, hand sprayers or airplanes.

Wettable powders are finely divided compositions comprising a particular carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (New York: Marcel Dekker, Inc., 1973), pages 79–84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculate sawdust, and granular carbon.

Microcapsules and other slow release formulations are advantageous as formulations to deliver and distribute the active ingredients. Microcapsules consist of fully enclosed droplets or granules containing the active materials in which the enclosing material is an inert porous membrane, arranged to allow escape of the enclosed materials to the surrounding medium at controlled rates over a specified period of time. Encapsulated droplets are typically about 1 to 50 microns in diameter. The enclosed liquid typically constitutes about 50 to 95% of the weight of the entire capsule, and may contain an amount of solvent in addition to the active materials. Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration or prilling are useful in the present invention as well as materials in their naturally occurring form. Examples of such carriers are vermiculite, starch sintered clay granules, kaolin, attapulgite clay, sawdust and granular carbon. Useful encapsulating materials include natural and synthetic rubbers, cellulosic materials, styrenebutadiene copolymers, polyacrylonitriles, polyacrylates, polyesters, polyamides, polyureas, polyurethanes and starch xanthates.

Emulsifiable concentrates consist of an oil solution of the formulant plus and emulsifying agent. Prior to use, the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

Formulations generally contain several additives in addition to the formulant and carrier or agent. Among these are inert ingredients, diluent carriers, organic solvents, water, oil and water, water in oil emulsions, carriers of dust and granules, and surface active wetting, dispersing and emulsifying agents.

The composition of the invention may comprise one or more compounds which possess biological activity.

Examples of useful complementary herbicides include:
1. Anilides
Alachlor-2-chloro-2',6'-diethyl-N-(methoxymethyl)acetanilide
Metolachlor-2-chloro-N-(2-ethyl-6-methylphenyl)-N-(2-methoxy-1 -methylethyl)acetamide
Propanil-N-(3,4-dichlorophenyl)propionanilide
Propachlor-2-chloro-N-isopropylacetanilide
Butachlor-2-chloro-2',6'-diethyl-N-(butoxymethyl)acetanilide
Acetochlor-2-chloro-N-(ethoxymethyl)-6'-ethyl-O-acetroboluidide
Metazachlor-2-chloro-2',6'-dimethyl-N-(1-pyrazol-1-yl methyl)acetanilide
2. Triazines
Atrazine-2-chloro-4-(ethylamino)-6-isopropylamino)-s-triazine
Cyanazine-2-chloro-4-(1-cyano-1-methylethylamino)-6-ethylamino-s-triazine
Metribuzin-4-amino-6-tert-butyl-3-(methylthio)-1,2,4 -triazin-5(4H)-one
Simazine-2-chloro-4,6-bis (ethylamino)-1,3,5-triazine
3. Thiocarbamates
Molinate-S-ethyl hexahydro-1H-azepine-1-carbothioate
Butylate-S-ethyl diisobutylthiocarbamate
EPTC-ethyl dipropylthiolcarbamate
Triallate-2,3,3-trichloroallyl-diisopropylthiolcarbamate
Diallate-cis-1-trans-2,3-dichloroallyl-diisopropylthiolcarboamate
Vernolate-S-propyl dipropylthiolcarbamate
4. Ureas
Monuron-3-(p-chlorophenyl)-1,1-dimethylurea
Linuron-3-(3,4-dichlorophenyl)-1-methoxy-1-methylurea
1-(1-cyclohexen-1-yl)-3-(2-fluoro phenyl)-1-methyl urea
3-[4-(4-halophenoxy)phenyl]-1,1-dialkylureas
5. Toluidines
Trifluralin -α,α,α-trifluoro-2,6 -dinitro-N,N-dipropyl-p-toluidine
Pendimethalin-N-(1-ethylpropyl)-3,4-dimethyl-2,6-dinitrobenzeneamine
6. Hormones
2,4-D -(2,4-dichlorophnoexy) acetic acid
MCPA-(2-methyl-4-chlorophenoxy) acetic acid
Dichlorprop-2,4,5-trichlorophenoxy acetic acid
MCPB-4-(4-chloro-2-methyl phenoxy)butynic acid
2,4,5-T-2,4,5-trichlorophenoxy acetic acid
Mecoprop-2-(4-chloro-2-methyl phenoxy)propionic acid and their derivatives
7. Diazines
Bentazon-3-isopropyl-1H-2,3,1-benzothiadiazin-4(3H)-one 2,2-dioxide
Oxadiazon-2-tert-butyl-4-(2,4-dichloro-5-isopropoxyphenyl)-Δ²-1,3,4-oxadiazolin-5-one
8. Diphenyl ethers
Acifluorfen-sodium 5-[2-chloro-4-(trifluoromethyl)phenoxy]2-nitrobenzoate
Fluazifop-butyl -(±)-butyl 2-[4[(5-(trifluoromethyl)-2-pyridinyl)oxy]phenoxy]propanoate
Chlomethoxynil-2,4-dichlorophenyl 3-methoxy-4-nitrophenyl ether
Sethoxydim-2[1-(ethoxyimino)butyl]-5-[2-(ethylthio)propyl]3-hydroxy-2-cyclohexen-1-one
9. Imidazolinones
Imazaquin-2-[4,5-dihydro-4-methyl-4-(1-methylethyl)-5-oxo-1H-imidazol-2-yl]-3-quinolin carboxylic acid
Imazethapur (±)-2-[4,5-dihydro-4-methyl-4-(1-methylethyl0-5 -oxo-1H-imidazol-2-yl]-5-et hyl-3-pyridinecarboxylic acid
10. Sulfonyl ureas
Bensulfuron methyl-methyl-2-[[[[[(4,6 -dimethoxypyrimidin-2-yl)amino]carbonyl]amino]sulfonyl]methyl]benzoate
Chlorimuron ethyl-ethyl2-(((((4-chloro-6 -methoxypyrimidin-2-yl)amino)carbonyl)amino)sulfonyl)benzoate
Chlorosulfuron-2-chloro-N-(4-methoxy-6-methyl-1,3,5-triazine2-yl)-amino carbonyl)benzene sulphoamide
Nicosulfuron-3-pyridimecarboxamide,2-[([4,6-dimethoxypyrimidin-2 -yl]amino-carbonyl)aminosulfonyl]-N,N-dimethyl
Primisulfuron-3-[4,6-Bis-(difluoromethoxy)-pyrimidin-2-yl]-1-(2-methoxycarbonylphenylsulfonyl)urea
Flumetsulam(proposed)-N-[2,6-difluorophenyl]-5-methyl(1,2,4)triazolo-[1,5a]-pyrimidine-2-sulfonamide
11. Dinitrophenols
DNOC-2methyl-4,6-dinitrophenol
Dinoterb-2-t-hidyl-4,6-dinitrophenol
12. Miscellaneous Compounds
Dimethazone-2-(2-chlorophenyl)methyl-4,4-dimethyl-3-isoxazolidinone
Norflurazon-4-chloro-5-(methylamino)-2-α,α,α-trifluoro-m-toly)- 3-(2H)-pyridazinone
Dalapon-2,2-dichloropropionic acid
Glyphosate-isopropyl amine salt of N-(phosphonomethyl)glycine
Fenoxaprop-ethyl-(+)-ethyl-2,4-((6-chloro-2 -benzoxazoloxy)phenoxy)propanoate
Organoarsenical herbicides such as MSMA-monosodium methanearsonate
Paraquat-1,1'-dimethyl-4,4'-dipyridylium ion
Pyridate O-(6-chloro-3- 3 phenyl-4-pyridazinyl)S-octyl carbonothioate
13. Benzoic acids
2,3,6-TBA-2,3,6-trichlorobenzoic acid
Dicamba-3,6-dichloro-2-methoxy-benzoic acid
Chloramben-3-amino-2,5-dichloro benzoic acid Alternatively, the compounds and compositions of this invention can be applied to a crop by addition to irrigation water supplied to the field to be treated. This method of application permits the penetration of the compositions into the soil as the water is absorbed therein.

As another alternative, the formulation can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers or airplanes.

Herbicide formulations of the types described above are exemplified in several illustrative examples below.

Example A

Dusts: The following substances are used to formulate a 5% dust:

5 parts of active substance
95 parts of talc

Example B

Granulate: The following substances are used to formulate a 5% granulate:

5 parts of active substance
0.25 part of epichlorohydrin
0.25 part of cetyl polyglycol ether
3.25 parts of polyethylene glycol
91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

Example C

Wettable powders: The following constituents are used to formulate (a) a 70%, (b) a 25%, and (c) a 25% wettable powder:

(a)
  70 parts of active substance
  5 parts of sodium dibutylnaphthylsulfonate
  3 parts of naphthalenesulfonic acid/phenolsulfonic acid/formaldehyde condensate (3:2:1)
  10 parts of kaolin
  12 parts of Champagne chalk
(b)
  25 parts of active substance
  4.5 parts of calcium ligninsulfate
  1.9 parts of Champagne chalk/hydroxyethyl cellulose mixture (1:1)
  1.5 parts of sodium dibutylnaphthalenesulfonate
  19.5 parts of silicic acid
  19.5 parts of Champagne chalk
(c)
  25 parts of active substance
  2.5 parts of isoctylphenoxy-polyethylene-ethanol
  1.7 parts of a Champagne chalk/hydroxyethyl cellulose mixture (1:1)
  8.3 parts of sodium aluminum silicate
  16.5 parts of kieselguhr
  46 parts of kaolin The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for treating parts of plants.

Example D

Emulsifiable concentrate: The following substances are used to formulate a 25% emulsifiable concentrate:

25 parts of active substance
2.5 parts of epoxidized vegetable oil
10 parts of an alkylarylsulfonate/fatty alcohol polyglycol ether mixture
5 parts of dimethylformamide
57.5 parts of xylene.

By diluting such a concentrate with water, it is possible to prepare emulsions of the desired concentrations, which are especially suitable for leaf application.

What is claimed is:

1. A herbicidal composition comprising
   (a) an herbicidally effective amount of a diphenyl ether of the formula

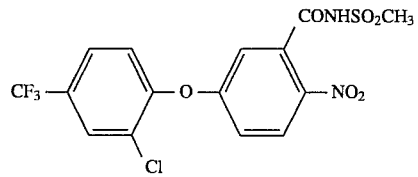

b) at least one nitrogen containing fertilizer that is present in an amount that increases the herbicidal activity of said diphenyl ether; and
   c) a crop oil concentrate.

2. A herbicidal composition according to claim 1 in which the fertilizer is urea ammonium nitrate wherein the % N is about between 28–33%.

3. A composition according to claim 1 wherein the crop oil concentrate is a vegetable oil containing a surfactant.

4. A composition according to claim 3 wherein said surfactant is a nonionic surfactant.

5. A composition according to claim 4 wherein the crop oil concentrate is a methylated sunflower oil containing 30% nonionic surfactant.

6. A method of controlling undesirable vegetation in the presence of a crop comprising the post-emergence application to the locus of said vegetation or said crop a herbicidal composition according to claim 1.

7. A method according to claim 6 in which the crop is soya.

* * * * *